United States Patent [19]

Chick et al.

[11] Patent Number: 5,116,493
[45] Date of Patent: May 26, 1992

[54] ARTIFICIAL PANCREATIC PERFUSION DEVICE WITH RESEEDABLE MATRIX

[75] Inventors: William L. Chick, Wellesley; Randall G. Rupp, Sterling, both of Mass.

[73] Assignee: W. R. Grace & Co.-Conn., New York, N.Y.

[21] Appl. No.: 674,698

[22] Filed: Mar. 25, 1991

Related U.S. Application Data

[63] Continuation-in-part of Ser. No. 398,739, Aug. 25, 1989, Pat. No. 5,002,661.

[51] Int. Cl.$^5$ .............................................. B01D 63/06
[52] U.S. Cl. ........................... 210/192; 210/209; 210/321.78; 210/321.87; 424/424; 435/284; 604/4; 604/175
[58] Field of Search .............. 210/192, 321.78, 321.87, 210/321.79, 321.88, 321.8, 321.89, 209, 198.1; 604/4, 175; 435/283, 284, 285, 286; 424/424, 520

[56] References Cited

U.S. PATENT DOCUMENTS

| | | | |
|---|---|---|---|
| 3,734,851 | 5/1973 | Matsumura | 210/321.75 |
| 3,827,565 | 8/1974 | Matsumura | 210/321.75 |
| 4,169,477 | 10/1979 | Bokros | 604/175 |
| 4,242,459 | 12/1980 | Chick et al. | 210/321.74 |
| 4,242,460 | 12/1980 | Chick et al. | 210/321.78 |
| 4,323,457 | 4/1982 | Sun et al. | 210/321.87 |
| 4,378,016 | 3/1983 | Loeb | 424/424 |
| 4,578,191 | 3/1986 | Jaffrin et al. | 210/321.87 |
| 5,002,661 | 3/1991 | Chick et al. | 210/192 |

FOREIGN PATENT DOCUMENTS

| | | |
|---|---|---|
| 0101373 | 2/1984 | European Pat. Off. |
| 0127989 | 5/1984 | European Pat. Off. |
| 7808199 | 3/1978 | France |
| 1479002 | 7/1977 | United Kingdom |
| WO85/05630 | 12/1985 | World Int. Prop. O. |

OTHER PUBLICATIONS

William L. Chick et al., (1975) *Science* 187:847–849.
William L. Chick et al., (1975) *Trans. Amer. Soc. Artif. Int. Organs* XXI:8–14.
Anthony M. Sun et al., (1977) *Diabetes* 26(12):1136–1139.
William L. Chick et al., (1977) *Science* 197:780–782.
A. D. Whittemore et al., (1977) *Trans. Amer. Soc. Artif. Int. Organs* XXIII:336–340.
P. M. Galletti et al., (1978) *Eur. Soc. Art. Organs* 5:132–135.
S. P. Naber et al., *Int. Congr. Series No. 500 Diabetes* 1979, pp. 227–231.
W. J. Tze et al. (1979) *Diabetologia* pp. 247–252.
N. J. Weinless and C. K. Colton (1983) *Ann. N.Y. Acad. Sci.* 413:421–423.
G. Reach et al., (1984) *Diabetes* 33:752–761.
C. K. Colton et al., "Development of Novel Semipermeable Tubular Membranes for a Hybrid Artificial Pancreas" pp. 541–555.
Y. Araki et al., (1985) *Diabetes* 34:850–854.
G. Reach et al., (1982) *Journees Annuelles de Diabetologie de l'Hotel-Dieu, Flammarion, Paris, at pp. 147–159.*

*Primary Examiner*—Robert A. Dawson
*Assistant Examiner*—Sun Uk Kim
*Attorney, Agent, or Firm*—Hamilton, Brook, Smith & Reynolds

[57] ABSTRACT

A device which serves as an artificial pancreas comprises a hollow fiber which is surrounded by islets of Langerhans enclosed in a housing. The islets are suspended in a semi-gel matrix or supporting material that is sufficiently viscous to physically support and maintain location of the islets about the hollow fiber, but sufficiently fluid to enable removal of the islet suspension from the device, followed by reseeding or replacement with fresh islet suspension. The matrix in which the islets are suspended preferably comprises calcium sodium alginate. The semi-gel supporting material also enables long term maintenance of islet cells in in vitro culture.

18 Claims, 4 Drawing Sheets

ARTIFICIAL PANCREATIC PERFUSION DEVICE WITH RESEEDABLE MATRIX

RELATED APPLICATION

The following is a Continuation-in-Part Application of U.S. patent application Ser. No. 07/398,739 filed on Aug. 25, 1989 for "Artificial Pancreatic Perfusion Device", now U.S. Pat. No. 5,002,661, and assigned to the assignee of the present invention. That Application is incorporated herein by reference.

BACKGROUND OF THE INVENTION

Beta cells, the insulin-producing cells of the pancreas, comprise more than 70% of the cell population found in discrete collections of cells in the pancreas which are known as islets of Langerhans. Some major effects of insulin are to increase the uptake of glucose by various tissues including muscle and fat and to decrease glucose output by the liver. Either absolute or relative insulin deficiency impairs glucose uptake and increases hepatic glucose output, thereby resulting in the abnormally high blood glucose concentrations characteristic of diabetes mellitus.

Insulin release from pancreatic islets is controlled by a combination of factors, including the concentration of glucose and other nutrients in the blood, gastrointestinal hormones and neuronal stimuli. In humans, glucose is the principal stimulus for insulin secretion from beta cells. However, other fuels such as amino acids and fatty acids also promote secretion.

Diabetes is generally characterized by an elevated concentration of glucose in the blood and urine. Insulin is administered to a diabetic patient in an effort to control or regulate the concentration of glucose and other nutrients in the blood. The objective of this regimen is to maintain glucose levels close to normal. One possible reason for the failure of this treatment to prevent the complications associated with diabetes is that daily insulin injections do not mimic the rapid insulin secretory responses of normal islets to physiological demand. Consequently, there has been a great deal of interest in developing a treatment for diabetics which would make it possible to maintain normal blood glucose levels at all times, an objective extremely difficult or impossible to achieve by insulin injections, diet and exercise.

Attempts have been made to produce an electromechanical artificial pancreas system comprised of, a glucose sensor, an information processor and an insulin pump to mimic physiological response patterns for insulin release. Thus far, this approach has not been effective.

Another approach to treating diabetes is replacement of the malfunctioning organ by transplantation of normal pancreatic tissue. However, transplantation of pancreatic tissue has met with limited success due to problems of tissue typing, donor availability and immune rejection.

To address these problems, researchers have focused on creating a hybrid artificial pancreas which mimics the organ's physiological response to glucose levels. Artificial pancreatic devices containing live islets have been designed to avoid immune rejection. These devices contain a semipermeable membrane which separates the transplanted islets from immunoreactive cells and molecules.

Matsumura describes an artificial pancreas device which includes a semipermeable membrane on one side of which once-dispersed live pancreatic islets are placed. (U.S. Pat. No. 3,827,565).

Sun et al. (U.S. Patent No. 4,323,457 (1982)) describe another artificial pancreatic device which is a container means through which a hollow fiber of 500 $\mu$m diameter is passed. The container holds pancreatic islets and the fiber is described as having a porosity which allows for passage of substances of molecular weight less than 100,000 Daltons.

Chick et al.: (U.S. Pat. Nos. 4,242,459 and 4,242,460 (1980)) describe a cell culture device having a generally circular fluid-tight cavity and a semipermeable tube wrapped about itself to form coils. Another cell culture device comprises a housing and a stationary spool about which a semipermeable tube is wrapped to form coils.

None of the presently-available artificial pancreatic devices solve the problems associated with diabetes and with implantation of an artificial device into an individual. Thus, there is a need for a pancreatic device containing viable islets of Langerhans which can be implanted into a diabetic individual and be effective in controlling blood glucose levels in such a way as to mimic normal physiological response to changing blood glucose concentrations. Although parent application U.S. Ser. No. 07/398,739 discloses one such device, that device does not provide for replacement of islets during in vivo use. Thus, there is a need for a pancreatic device in which islets can be removed from the device and replaced with fresh islets at various times during use, for example upon a drop in insulin output.

SUMMARY OF THE INVENTION

The present invention relates to an artificial organ perfusion device, in particular an artificial pancreatic perfusion device which results in the secretion of insulin into the blood of an individual in response to changes in blood glucose concentrations. The device employs a hollow fiber for passage of blood through a housing which contains pancreatic islets of Langerhans in an appropriate supporting material and a connecting means for connecting a blood vessel, such as a vein or an artery, to the ends of the hollow fiber to provide continuous flow from the individual, through the device and back into the individual.

The islets are introduced into the housing suspended in a supporting material which physically distributes and maintains position of the islets about the length of the hollow fiber. According to the present invention, the supporting material (or matrix) is a substance that is sufficiently viscous to physically support and maintain location of the islets about the fiber but sufficiently fluid to enable removal of the supporting material, with the islets, from the housing. Hence, the supporting material of this invention renders the device reseedable (i.e., enables substitution of islets by replacement of the islet suspension or portion thereof). Preferably the supporting material comprises calcium sodium alginate or similar semi-gel (gel-like) media or matrixes. Preferably this matrix has a viscosity of about 900 to 1000 centipoises at 37° C.

In addition, the supporting material aids maintenance of islets in culture. In this use, the supporting material preferably includes islet cell culture medium and islet cells to form an islet mixture. The islet suspension is prepared from the islet mixture, for introduction into an artificial pancreatic device, by centrifuging to form a culture medium phase and an islet suspension phase.

The culture medium phase is removed, and the device is seeded with the remaining islet suspension phase.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3b is a plan view of the embodiment of FIG. 3a.

DETAILED DESCRIPTION OF THE PREFERRED EMBODIMENT

The present invention relates to a device useful for controlling fluctuations in blood glucose levels, as well as to a method of treating such fluctuations, particularly in individuals with diabetes. The device includes viable intact pancreatic islets of Langerhans, islet fragments, beta cells, or a combination thereof, which sense and respond to blood glucose levels as blood flows through a hollow fiber which selectively allows passage of molecules having a molecular weight of less than about 100,000 Daltons. The term hollow fiber is meant to encompass various hollow, tissue compatible materials capable of transporting a medium (i.e., blood) and having a selected porosity which selectively allows the passage of substances across the material.

Figure 1:
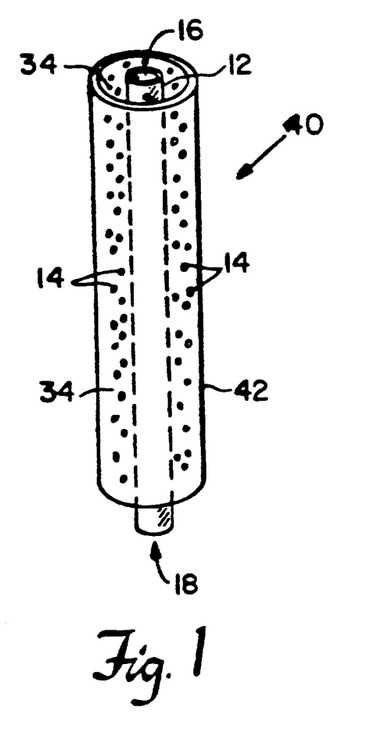
FIG. 1 is a schematic view of an artificial pancreatic perfusion device generally embodying the present invention.

An artificial pancreatic perfusion device embodying the present invention is illustrated in FIG. 1 and generally referenced as 40. The device provides a hollow fiber 12 surrounded by islets of Langerhans 14.

Blood from an individual enters hollow fiber 12 through inlet end 16 and flows within hollow fiber 12, along the length of fiber 12 toward outlet end 18. Hollow fiber 12 is a porous membrane with pore size which selectively allows transverse passage of substances having a molecular weight of less than about 100,000 Daltons. Thus, the pores allow diffusion of glucose and necessary nutrients from the blood through the walls of hollow fiber 12 to islets 14 as the blood flows along the length of the fiber 12. In response to the provided glucose and nutrients, the islets 14 generate and secrete insulin, which diffuses from outside of hollow fiber 12 through the walls of the fiber and into the blood flowing therethrough. The insulin-containing blood (i.e., blood flowing from the device) exits fiber 12 at outlet end 18 to provide the generated insulin to the individual.

Specifically, in in vivo use of device 40, one end of hollow fiber 12 is connected by connecting means to a blood vessel, such as an artery, for receiving blood, and the opposite end of fiber 12 is connected by connecting means to a second blood vessel, such as a vein, for providing insulin-containing blood to the individual. For ex vivo use of device 40, connections other than to an artery and vein are suitable as long as blood or other medium flows through hollow fiber 12 from inlet end 16 to outlet end 18. The connecting means can be comprised of any one of various tissue compatible materials such as vascular graft material. The ends of the hollow fiber can be connected by connecting means to a single blood vessel, such as an artery or vein. Alternatively, the ends of the hollow fiber can be connected by connecting means to two blood vessels, such as an artery and a vein as described above.

Preferably, hollow fiber 12 is a porous acrylic copolymer membrane of about 100,000 Dalton average porosity, such as the type XM, manufactured by the Amicon Division of W. R. Grace & Co., Conn. The pore sizes selected provide a barrier to protect the xenograft from a host immune reaction. A pore size is selected on the basis that the fiber must retain >90% of an IgG solution. As a result of this protective barrier, the islets can be obtained from a variety of mammalian sources, such as canine, bovine, porcine, or human pancreatic tissue, without necessarily requiring immunomodulation of the islets or immune suppression of the recipient.

The ends of the hollow fiber are connected to a blood vessel or vessels in such a way that the inner diameter of the fiber substantially matches the inner diameter of the blood vessel, to provide smooth and continuous flow of blood. A fiber having an inner diameter which substantially matches the inner diameter of the vessel can be employed. For example, hollow fiber 12 has a uniform inner diameter of about 4 mm to about 7 mm. Such a diameter is compatible with the inner diameter of an individual's arteries and veins to which ends of fiber 12 are to be connected in in vivo use of the device. As a result, the potential for clotting at vascular connective junctions is reduced. Alternatively, the hollow fiber can have an inner diameter which differs from that of a blood vessel. For example, the hollow fiber can be adapted with a connecting means which at one end substantially matches the diameter of the vessel and at an opposite end substantially matches the diameter of the fiber, thus providing smooth and continuous flow of blood from the blood vessel and into the device.

In addition, the connecting means can comprise a butt joint providing a smooth, essentially step free internal transition between the vessel and the fiber 12. The butt joint is made using a mandrel which can be either rigid or made of a deformable material. The mandrel is placed in the fiber and graft lumen to match the internal diameters. A smooth rigid rod can be utilized as a mandrel. The rod must have a tapered end that fits tightly into the lumens of both the fiber and graft. A deformable material that will expand when compressed can also be used as a mandrel. This can be placed in the lumens of the fiber and graft and expanded. The expanded material will tightly fit the graft and fiber creating a gradual transition between the fiber and graft. Once in place, adhesive can be cast around the mandrel between a slight gap left between the fiber and graft. Upon curing the mandrel can be removed and a smooth internal transition between the fiber and graft will remain.

The fiber has a wall thickness of 100-200 microns and a length sufficient to provide an inner surface area of the fiber of greater than about 60 cm$^2$, where the inner surface area of hollow fiber 12 equals the product of the length of the fiber, the inner diameter of the fiber and $\pi$. For example, an inner surface area of about 60 cm$^2$ or greater makes it possible to maintain the number of islets needed to produce the required amount of insulin. For example, for implantation into a human subject, the inner surface area of the hollow fiber can be about 100 cm$^2$ and the length of the fiber can be about 56 cm, which has been shown to be sufficient to support about 300,000 islets in vitro.

The islets 14 are introduced or seeded into the device in such a manner that the islets are distributed about hollow fiber 12. In order to insure proper distribution of islets about hollow fiber 12 and maintain the islets 14 in the desired locations about hollow fiber 12, an appropriate supporting material, such as a semi-gel matrix, that forms a suspension of the islets (referred to as an islet suspension) is used. The supporting material can be comprised of various substances which are capable of maintaining islet viability and physically supporting the islets in suspension.

For example, in one embodiment, a semi-gel matrix is formed by adding islets to a solution of nutrient medium and calcium sodium alginate dissolved in water. The semi gel matrix is sufficiently viscous to physically suspend and support the islets and yet sufficiently fluid to be pipettable (i.e., removable from and injectable into the device by suitable means such as by vacuum). Specifically, the semi-gel matrix has a viscosity in the range of about 900 to 1000 centipoises at 37° C., and thus has a consistency between a liquid and semi-solid. As a result, the islet suspension can be introduced into the device in a manner such that islets are distributed and maintained about the outside of fiber 12. The islet suspension maintains fluidity and is removable by suction means such as a syringe or the like. This allows the device to be easily reseeded with fresh islets 14 as necessary or desired, unlike the previously taught semi solid alginate or agar matrix which do not maintain fluidity and hence are not easily removable from the device. Such reseeding is advantagous in prolonging the operating life of the device. It is understood that other similar pipettable viscous matrices may be employed as the supporting material to provide a reseedable artificial pancreatic perfusion device.

The islet suspension also allows storage under in vitro culture conditions (e.g., 37° C.) to maintain the islets. To use for storage, the islet suspension comprises islet cell culture medium. The term "islet mixture" is used herein to refer to the supporting material/islet/culture medium mixture. The term "islet suspension" is used herein to refer to the supporting material/islet mixture without culture medium, although the islet suspension may contain other components, as described below.

To process the islet mixture from culture for device use, the islet mixture portion is centrifuged to form a culture medium phase and an islet suspension phase. The culture medium phase is removed and the remaining islet suspension phase is introduced into the device for use to produce insulin. After a desired period of use, subsequent amounts of islet mixture from culture may be similarly processed and used in the device, each subsequent islet suspension portion being substituted for some or all of the islet suspension in the device. Each islet suspension portion or subsequent portion should be in an amount sufficient for the production of a desired amount of insulin by the device.

The housing can be comprised of plastic (e.g., polyacrylic), stainless steel, titanium or other implantable metallic substance. For example, the housing can be polycarbonate, polysulfone, polymethyl methacrylate or mixtures thereof. The housing must be tissue compatible and sufficiently inflexible to protect hollow fiber 12 and is preferably lightweight. In the embodiment illustrated in FIG. 1, extruded plastic housing 42 is generally cylindrical in shape and is as long as hollow fiber 12. Housing 42 coaxially encompasses hollow fiber 12, which lies substantially straight and curveless within housing 42. Inner walls of housing 42 form a chamber 34 about the outer surface of fiber 12. Preferably, the islet suspension is distributed circumferentially and longitudinally along the length of hollow fiber 12 in this chamber 34.

Figure 2:
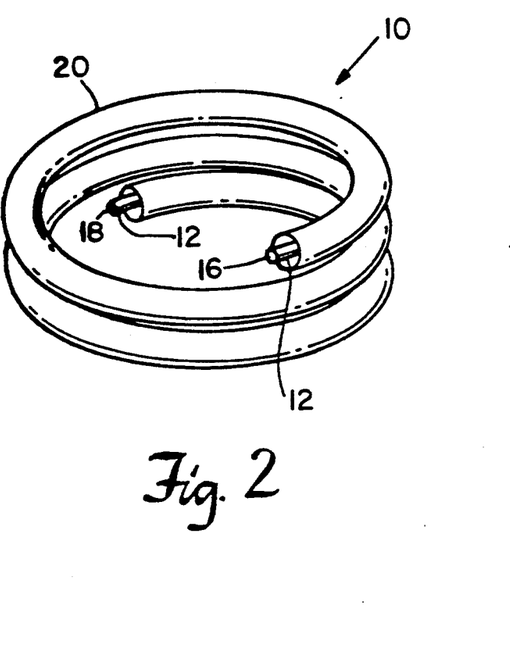
FIG. 2 is a schematic view of another artificial pancreatic perfusion device embodying the present invention and having a coiled housing.

In the embodiment shown in FIG. 2, housing 20 is generally tubular in shape and follows the contour of hollow fiber 12 which is, for example, about 22 inches long. More specifically, housing 20 is coaxially positioned about fiber 12 along the length of fiber 12 and housing 20 together with fiber 12 are coiled about a longitudinal axis to provide a space saving compact device 10. In such a configuration, inner walls of housing 20 form a chamber about the outer surface of hollow fiber 12. It is into this chamber that the islet suspension is introduced such that fiber 12 is surrounded along its length by islets 14.

Figure 3A:
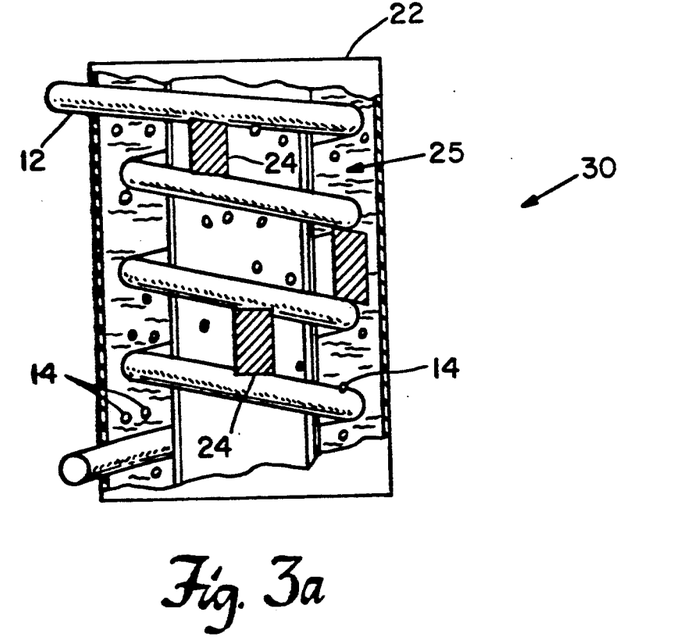
FIG. 3a is a schematic view partially cut away of another embodiment of the present invention having an annular housing.
Figure 3B:
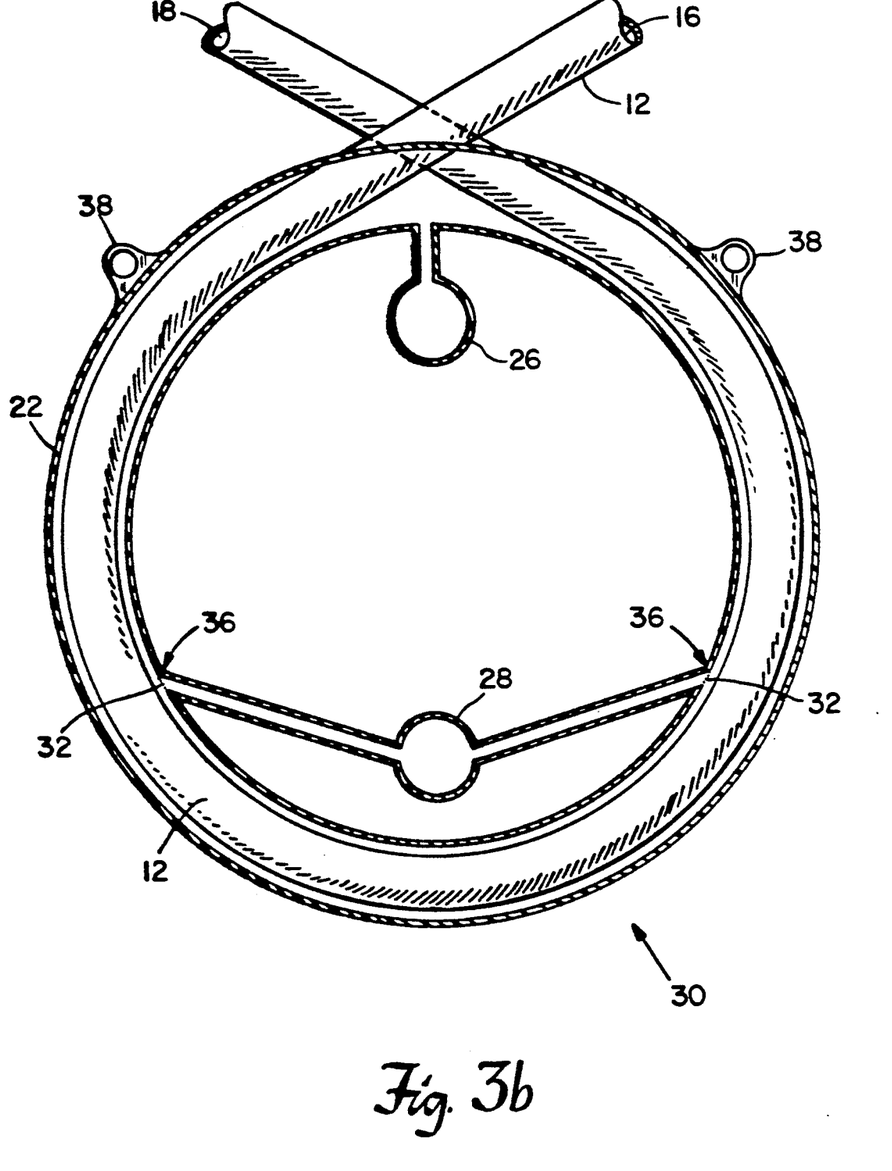

A preferred embodiment of the present invention is illustrated in FIGS. 3a and 3b and is generally referenced 30. Hollow fiber 12 is coiled into one or more loops about a longitudinal axis, and the coiled fiber is enclosed in an annular shaped housing 22. In this configuration, each loop formed by hollow fiber 12 within housing 22 may be spaced apart from a preceeding and succeeding loop by spacers 24. The spacers 24 ensure a gap 25 between each loop of fiber 12 and ultimately enable the islet suspension to be positioned circumferentially along the length of hollow fiber 12. To that end, the islet suspension is introduced into annular housing 22 in a manner which substantially fills gaps between loops of hollow fiber 12 as well as areas around the inner and outer curves of each loop, such that the islet suspension and thus islets 14 surround fiber 12 along its length.

In addition, housing 22 includes injection ports 26 and 28 as shown in FIG. 3b. These ports aid in the introduction of the islet suspension into the housing in such a manner that it surrounds coiled hollow fiber 12 within the housing 22. In the present invention, the suspension is drawn through one port 26 by negative pressure generated at the other port 28.

More specifically, a syringe containing the islet suspension is positioned, as for injection, at port 26. Means for drawing air from housing 22, such as a second syringe, is positioned at port 28. The drawing means is operated so as to withdraw air from housing 22 through port 28 and thus create a current directed from port 26 through housing 22 and out port 28. Consequently, the negative pressure pulls the islet suspension from the first syringe through port 26 and into housing 22, and toward port 28.

To prevent the suspension from being withdrawn from housing 22 through port 28 once drawn into the housing, screens 32 can be attached to cover internal openings 36 of port 28. For example, screens 32 comprise a tissue compatible mesh material with apertures sufficient to prevent islets from being withdrawn (i.e., smaller than the islets). For example, screens with 20-30 micron wide apertures such as of the Nytex ® brand or similar type can be used. Screens 32 are fastened to the inner walls of housing 22 over openings 36 by common methods and means, including tissue compatible epoxies.

Furthermore, hollow fiber 12 exits the annular shaped housing 22 so that one end 16 of hollow fiber 12 is connected to a blood vessel, such as an artery, in such a manner that blood flows into, through and out of the device. An opposite end 18 of hollow fiber 12 is connected to a second blood vessel, such as a vein, for providing insulin-containing blood to an individual, as described in FIG. 1.

The annular shaped housing 22 may also provide one or more suture sites 38, through which the device 30 is anchored to the individual.

In an alternative embodiment to the device 30 of FIGS. 3a and 3b, the annular housing is designed to be particularly lightweight. Such a lightweight annular housing is illustrated in an exploded view in FIG. 3c and is described below.

Figure 3C:
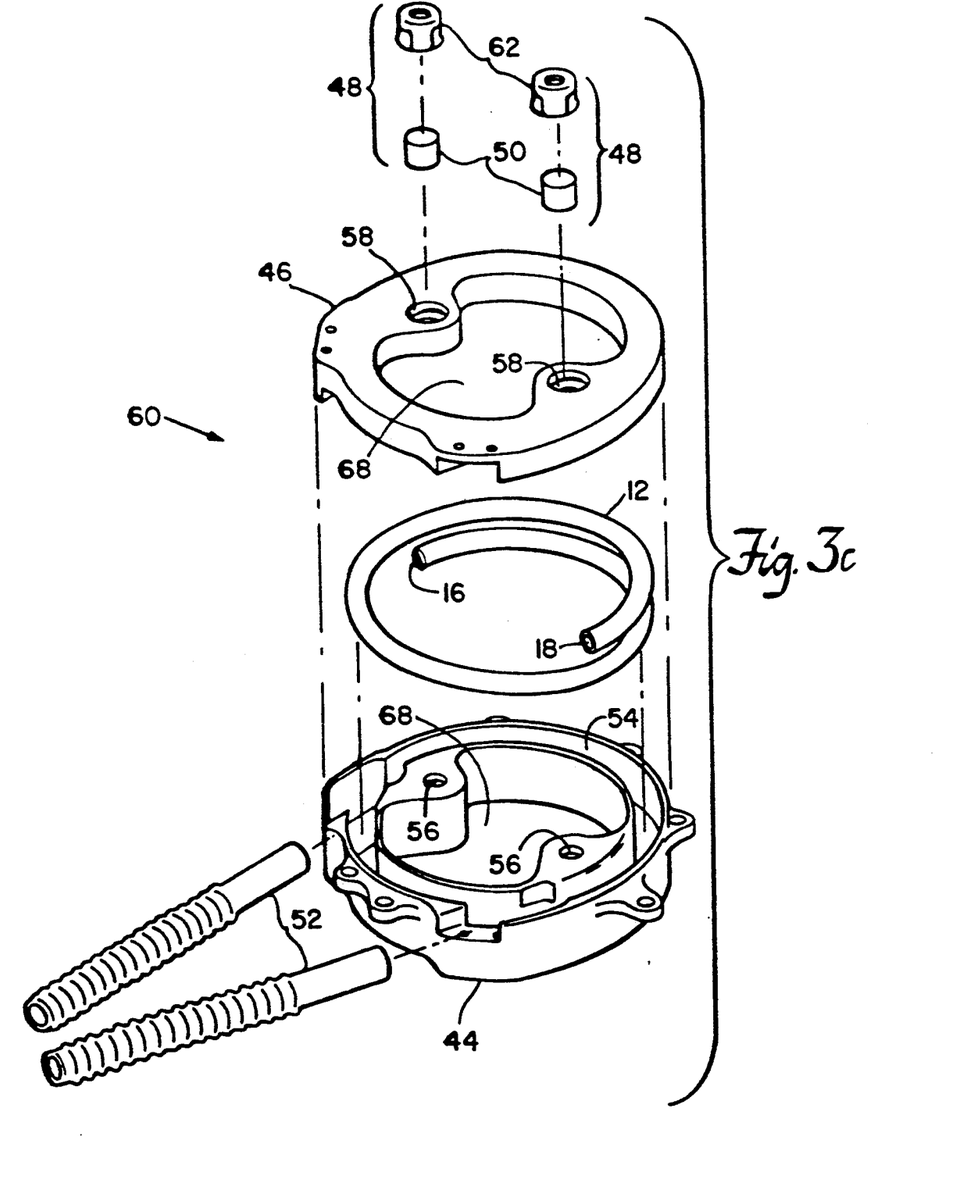
FIG. 3c is an exploded view of another embodiment having a lightweight annular housing.

A bottom half 44 is machined from acrylic with a FIG. 8 central cavity 68, an inner circumferential groove 54, two bores 56 (preferably 1/16 inch diameter) leading into the circumferential groove 54 and suture sites 64 about the exterior. The hollow fiber 12 sits coiled in groove 54 with ends 16 and 18 attached to connecting means, such as vascular grafts 52 for in vivo use of the device 60. Further, the housing bottom half 44 is shaped to accommodate vascular grafts 52 connected to the fiber ends 16 and 18 to allow these grafts to protrude from the housing. In addition, a butt joint can be made using a mandrel as described previously to provide a smooth, essentially step free internal transition between the fiber and graft lumen. Optionally, a screen, such as the screen 32 described in FIG. 3b, can be attached to the wall of groove 54 to cover the opening of bore 56 in the groove to prevent drawing of islets out of the housing during introduction of the islet suspension into the housing.

A housing top half 46 is machined from acrylic with a FIG. 8 central cavity 68, openings 58 and an inner circumferential groove which match respectively the FIG. 8 central cavity 68, bores 56 and inner groove 54 in bottom half 44. Housing top half 46 is welded or otherwise hermetically sealed to bottom half 44 with respective matching parts aligned. Snapped into openings 58 are injection port assemblies 48. Each injection port assembly 48 includes a silicon plug 50 inside a cap 62, as is common in the art. The port assemblies 48 positioned in openings 58 provide the injection ports or sites for introducing the islet suspension to hollow fiber 12 coiled within the housing inner groove 54. Alternatively, injection sites could be welded into either the housing top half 46 or bottom half 44.

After the housing top half 46 and bottom half 44 have been welded together, a tissue compatible adhesive is applied to where the housing meets the connecting means to ensure a hermetic seal. Epoxy of medical grade, such as T674 manufactured by Emerson and Cumings, Inc. (Polyfibron Division of W. R. Grace & Co., Conn.), is preferred.

Because of the central cavity, the device 60 with the islet suspension surrounding fiber 12 weighs about 40 grams. Planar covers, of silicon or like material, for the top and bottom sides of the housing cover the FIG. 8 central cavity and prevent fluid from building up within the cavity during in vivo use of the device 60 without adding substantial weight. Such covers are attached to the respective outer surfaces of housing top half 46 and bottom half 44 by welding, adhesive or other methods and means common in the art.

It is understood that other configurations of the present invention are possible. Such configurations need only ensure the distribution of islets about hollow fiber 12, preferably circumferentially and longitudinally about fiber 12, such that fiber 12 is surrounded along its length by the islets 14. In optimizing the design of a configuration, it is understood that the distance between the islets and hollow fiber 12 needs to be minimized to maximize diffusion of substances, including substances which stimulate insulin secretion, as well as nutrients and oxygen, from the blood to the islets.

Preparation of islets and their introduction into the device is carried out as follows. Pancreatic islets of Langerhans are isolated from any one of various mammalian pancreatic tissues, for example canine, bovine, porcine, or human. The term "islet" or "islets" as used herein includes the constituent cell types within the islet of Langerhans, including beta cells, the actual producers of insulin, intact islets, islet fragments or combinations thereof. The procedure for isolating islets from the exocrine tissue of the donor pancreas is described in Example I.

Islets of Langerhans are suspended in an appropriate supporting material. One such supporting material includes calcium sodium alginate. Additional components, such as collagen and laminin and/or growth factors can be added to the islet suspension. For example, approximately 100 $\mu$g/ml of collagen I, approximately 80-100 $\mu$g/ml of collagen IV and approximately 5-10 $\mu$g/ml of laminin can be added to the islet suspension.

The islet suspension can also contain other cells which enhance islet viability. The presence of endothelial cells or fibroblasts can create an environment more like that in which islets occur naturally. Other cell types which produce growth factors or basement membrane components can be cultured with the islets to enhance growth and viability. In addition, an endothelial cell layer at the graft site can contribute to increased patency of the anastomosis site.

The invention provides a method for seeding an artificial pancreatic perfusion device with a suspension of islets of Langerhans prior to use of the device. The invention also provides a method for reseeding the device with fresh islet suspension on one or multiple occasions following use of the device for insulin production. In the seeding or reseeding process, the semi-gel islet suspension is introduced to the outside of hollow fiber 12 as described previously in conjunction with FIG. 3b. The semi-gel matrix suspends the islets in their respective locations about hollow fiber 12 while remaining sufficiently fluid during use of the device to enable easy removal and substitution of the islet suspension on further occasions as necessary. For example, reseeding may be indicated after a decrease in insulin production by the device.

Inlet end 16 and outlet end 18 are attached to connecting means, such as vascular graft material, for example polyurethane, polytetrafluoroethylene, or Dacron TM (EI duPont de Nemours & Co.). The inlet end 16 graft material is surgically connected to a blood vessel and the outlet end 18 graft material is surgically connected to a second blood vessel, and blood flow is established through the fiber by means well known in the art.

Preparation of the islet suspension, and the seeding and reseeding protocol in a preferred embodiment is as follows. Islets of Langerhans are added to a solution of calcium sodium alginate and cell culture medium (hereinafter alginate/medium solution), forming an islet mixture. For use in the seeding or reseeding of the device, the islet mixture is centrifuged to form a culture medium phase and an islet suspension phase. The culture medium phase is removed and the islet suspension phase is used in one or more portions to seed and/or reseed an artificial pancreatic device of the present invention. Further details of the foregoing procedure are found in Prospective Example A. In an alternative embodiment, where no storage of islets is required prior to seeding or reseeding, the islet suspension may be formed directly by adding islets to a calcium alginate solution (i.e., without including cell culture medium).

Another application for the alginate/medium solution is the long term maintenance of islets in culture. A difficulty encountered in maintaining islets in culture is that they attach to the tissue culture plastic of the chambers in which they are maintained. Once attached they are difficult, if not impossible, to remove from the plastic and use for experiments or perfusion device seeding. By mixing the islets with the alginate/medium solution, an islet mixture is formed which suspends the islets as well as provides nutrients to enable the islets to be maintained in culture for extended periods.

The islet mixture and islet suspension can easily be transferred from vessel to vessel without adversely affecting islet function. Consequently, the islet mixture can be used both to maintain islets in culture and as a basis from which to prepare the islet suspension for the artificial pancreatic perfusion devices described above. For this purpose, the islet mixture is formed as described above and maintained in in vitro culture. A first portion of islet suspension is obtained for use in a device by centrifugation of a first amount of the islet mixture and separation of the resulting culture medium-phase from the islet suspension phase. The islet suspension phase is injected into and used in the artificial pancreatic perfusion device for the production of insulin for a desired period of time. A second amount of the islet mixture is subsequently taken from culture and centrifuged to prepare a second portion of islet suspension which is used to reseed the device after removal of all or part of the first portion of islet suspension. Other amounts of the islet mixture are similarly taken from culture and centrifuged to prepare further islet suspension portions used to reseed the device on multiple occasions for the continued production of insulin by the device.

It is understood that the islet mixture and islet suspension of this invention may be used in a variety of in vitro or in vivo devices which require a supporting material to distribute and maintain the position of islets, and for which it may be desired to replace all or a portion of the islet suspension following a period of use. It is further understood that the cell culture medium is required to maintain the islets in culture prior to placing them in an in vivo or in vitro device, but that cell culture medium is not required where the isolated islets will be used immediately in a device which will maintain their viability. After the cells are placed in a device, islet viability is maintained by cell culture medium or blood being perfused through the device.

EXAMPLE I

Isolation of Islets From Pancreatic Tissue

Islets of Langerhans were obtained from pancreata of donor animals (e.g., dog, cattle, pig). Islets of Langerhans were isolated and purified by a modification of published procedures, Moskalewski, S., *Gen. Comp. Endo.*, 5:342 (1965); Lacy P. E. and M. Kostianovsky, *Diabetes*, 16:35 (1967); Lacy, P. E. et al., *Diabetes*, 31 (*Suppl.* 4):109 (1982). Briefly, the pancreas was infused via the pancreatic duct with a suspension of collagenase which digested connective tissue and disrupted the integrity of the gland. The gland was further dissociated by shaking with marbles until tissue fragments were reduced to a size of less than 500 microns diameter. This disassociation procedure released islets from the exocrine tissue that surrounded them. Islets were then separated from non-islet tissue by centrifugation on a discontinuous gradient of Ficoll TM (Pharmacia Fine Chemicals, Inc.) (27% w/v; 23.5% w/v; and 11% w/v), which utilized the difference in density of cell types to permit islets (lower density) to be positioned at the interface of the 11% and 23.5% Ficoll layers, while non islet tissue separated under centrifugation. Islets were collected, washed, and plated into culture plates until used.

EXAMPLE II

In vitro Culture of Islets

Figure 4:
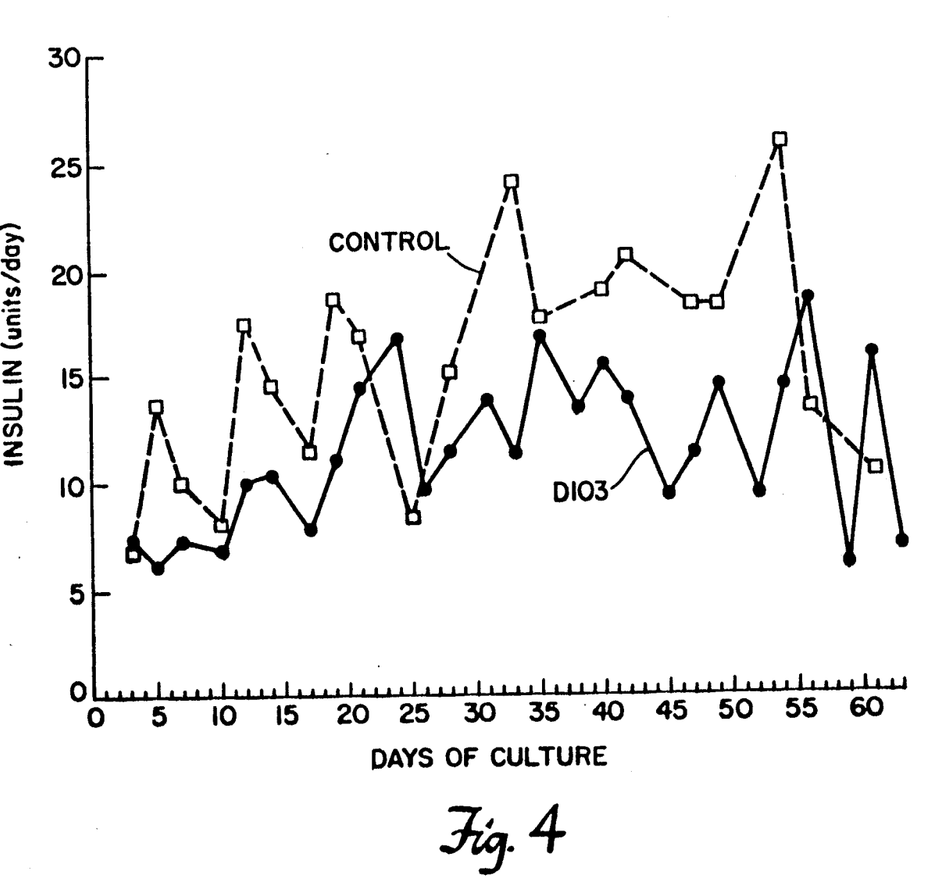
FIG. 4 is a graphic representation of insulin producing islet viability in culture in a calcium sodium alginate matrix of the present invention.

An islet pellet was obtained by from the culture plates of Example I collecting isolated islets, centrifuging and removing culture medium by pipetting. To this pellet, a 1% solution of calcium sodium alginate and cell culture medium was added. For use of 6-well plates in which each well held no more than 10 ml, 8 to 10 ml of alginate/medium solution was added to the islet pellet for each well to create an islet mixture. Three plates were prepared and were stored at about 37° C. A sample was taken from each plate about every 2 or 3 days and insulin output was measured by radioimmunoassay. The medium was completely changed at the time of taking of the samples, by centrifuging, then removing the cell culture medium phase and mixing the resulting islet suspension with fresh cell culture medium. A calculation of the daily production of insulin was then performed. For islet mixtures containing 2,000 islets per well, insulin production averaged about 0.4 unit/day over a period of 22 days. For islet mixtures containing 8,000 islets per well, insulin production averaged about 1.0 unit/day over a period of 22 days For islet mixtures containing 30,000 islets per well, insulin production averaged about 1.6 units/day over a period of about 22 days. Data from the three plates are shown in FIG. 4 and demonstrate that at 2,000, 8,000 and 30,000 islets per well in alginate/medium solution, the islets can be maintained for at least 22 days and continue to produce insulin. It is important to note that all of these islets remained suspended in the islet mixture in the tissue culture plates and that none became attached to the plastic plates.

PROSPECTIVE EXAMPLE A

Semi-gel Preparation and Reseeding Protocol

One gram of calcium sodium alginate (Kelcosol TM, Kelco Corp.) is wrapped in aluminum foil and autoclaved for 15 minutes. This one gram of powder is added to 100 ml of cell culture medium and stirred until completely dissolved (approximately 1 hour) to form a 1% weight per volume alginate/medium solution. In a separate 15 ml culture tube, 200,000 islets are pelleted by gentle centrifugation. Culture medium is decanted from the pelleted islets and approximately 14 ml of the alginate/medium solution is added. After gently mixing the islets with alginate/medium solution to form a homogeneous islet mixture, the islet mixture is centrifuged at 1500× g for five minutes to form two layers. The bottom layer (approximately 5 ml) contains the viscous alginate and islets (the islet suspension of the present invention), and the top layer consists of the culture medium. The culture medium is removed by pipetting, and the remaining islet suspension is used to seed a perfusion device. The islet suspension has a viscosity in the range of about 900 to 1000 centipoises at 37° C.

The islet suspension is seeded through injection ports as in FIGS. 3b and 3c, or distributed by some other means. The seeded device is then ready for implantation into a desired subject. After a period of device use, such as several days to months or upon a decrease in insulin output or the like, the device is reseeded with the islet suspension described above The reseeding includes removal of the first portion of islet suspension introduced into the device. Such removal is by suction, such as by a syringe, through injection ports 26, 28 shown in FIGS. 3b and 3c. The substituting portion of islet suspension is then seeded through the injection ports as previously described. It is understood that other intermediate steps may be taken between the removal of the initial portion of islet suspension and the introduction of the substituting portion of islet suspension, such as flushing or other cleaning procedures.

Equivalents

While this invention has been particularly shown and described with references to preferred embodiments thereof, it will be understood by those skilled in the art that various changes in form and details may be made therein without departing from the spirit and scope of the invention as defined by the appended claims.

We claim:

1. An artificial pancreatic perfusion device for providing insulin to an individual, the device comprising:
    a) a hollow fiber having one end connected to a blood vessel through a connecting means to receive blood from the individual and an opposite end connected to a blood vessel through a second connecting means to return blood to the individual, the hollow fiber having a porosity which selectively allows substances to pass transversely therethrough, such that blood flows within the hollow fiber, along the length of the fiber; and
    b) a housing containing a suspension of pancreatic islets of Langerhans, the suspension including pancreatic islets distributed in a supporting material about the hollow fiber such that the hollow fiber is surrounded by pancreatic islets along its length, the supporting material characterized by (i) being sufficiently viscous to maintain distribution of the islets with respect to the hollow fiber, and (ii) being sufficiently fluid to enable removal of the islet suspension for subsequent replacement thereof.

2. An artificial pancreatic perfusion device as in claim 1 wherein the islet suspension is removable from the housing by suction means.

3. An artificial pancreatic perfusion device as in claim 1, wherein the supporting medium has a viscosity of about 900 to about 1000 centipoises at 37° C.

4. An artificial pancreatic perfusion device as in claim 1 wherein the supporting material comprises calcium sodium alginate.

5. An artificial pancreatic perfusion device as in claim 1 wherein the islet suspension further includes at least one of collagen, laminin and growth factors.

6. In an artificial pancreatic perfusion device for providing insulin to an individual, the device comprising (i) a hollow fiber with a porosity that selectively allows substances to pass transversely therethrough and (ii) a housing containing a suspension of pancreatic islets of Langerhans about the hollow fiber, the improvement comprising:
    a matrix in which the islets are distributed and suspended to form an islet suspension, the matrix being sufficiently viscous to physically suspend and maintain the islets about the hollow fiber and sufficiently fluid to enable removal of the islet suspension for subsequent replacement thereof.

7. An artificial pancreatic perfusion device as in claim 6 wherein the matrix is a semi-gel.

8. An artificial pancreatic perfusion device as in claim 6 wherein the matrix has a viscosity of about 900 to about 1000 centipoises at 37° C.

9. An artificial pancreatic perfusion device as in claim 6 wherein the matrix includes calcium sodium alginate.

10. An artificial pancreatic perfusion device as in claim 6 wherein the matrix maintains sufficient fluidity during use to enable removal of a portion of the islet suspension subsequent to a period of use.

11. A method for seeding a device with islets of Langerhans on multiple occasions before and after use of the device for the production of insulin, comprising the steps of:
    (a) forming an islet suspension by distributing the islets in a supporting material sufficiently viscous to physically suspend the islets and sufficiently fluid to enable removal of the islet suspension from the device as desired;
    (b) introducing a first portion of islet suspension into the device, such first portion sufficient for the production of a desired amount of insulin by the device;
    (c) withdrawing some or all of said first portion of islet suspension from the device following a period of use of the device; and
    (d) introducing a second portion of islet suspension into the device, such second portion sufficient for the production of a desired amount of insulin by the device.

12. A method for seeding as in claim 11 wherein the step of forming the islet suspension includes:
    (i) preparing an islet mixture comprising islets, supporting material and cell culture medium;
    (ii) maintaining said islet mixture in in vitro culture; and
    (iii) processing the islet mixture to obtain islet suspension for use in the steps of introducing the islet suspension into the device in steps (b) or (c).

13. A method for seeding as claimed in claim 12 wherein the islet mixture is maintained in culture at about 37° C.

14. A method for seeding as claimed in claim 12 wherein the islet mixture is processed to obtain islet suspension for introduction into the device by centrifuging such that a culture medium phase and an islet suspension phase are formed, and removing the culture medium phase to isolate the islet suspension phase.

15. A method of seeding as claimed in claim 11 wherein the device is an artificial pancreas device.

16. A method of preparing islets of Langerhans for use in a device, comprising the steps of:
(a) providing islets;
(b) combining the islets with cell culture medium and a sufficient amount of a supporting material to form an islet mixture, the supporting material being sufficiently viscous to maintain suspension of the islets and sufficiently fluid to enable removal of the islet suspension from the device;
(c) storing the islet mixture under in vitro culture conditions suitable for maintaining islets; and
(d) forming a pipettable islet suspension phase from an amount of the islet mixture, by removing the cell culture medium from the islet mixture.

17. A method of preparing islets as claimed in claim 16 wherein the supporting material comprises calcium sodium alginate.

18. A method of preparing islets as claimed in claim 16 further comprising the steps of:
removing islet mixture from in vitro culture;
centrifuging the islet mixture to form a culture medium phase and an islet suspension phase; and
isolating the islet suspension phase for use in the device.

* * * * *